US005591162A

United States Patent [19]
Fletcher et al.

[11] Patent Number: 5,591,162
[45] Date of Patent: *Jan. 7, 1997

[54] TREATMENT METHOD USING A MICRO HEAT PIPE CATHETER

[75] Inventors: Leroy S. Fletcher, College Station, Tex.; George P. Peterson, West Springfield, Va.

[73] Assignee: The Texas A&M University System, College Station, Tex.

[*] Notice: The term of this patent shall not extend beyond the expiration date of Pat. No. 5,190,539.

[21] Appl. No.: 215,276

[22] Filed: Mar. 21, 1994

Related U.S. Application Data

[60] Division of Ser. No. 994,551, Dec. 21, 1992, Pat. No. 5,417,686, which is a continuation-in-part of Ser. No. 550,519, Jul. 10, 1990, Pat. No. 5,190,539.

[51] Int. Cl.⁶ ..................................... A61B 17/36
[52] U.S. Cl. .............................. 606/25; 606/28
[58] Field of Search ..................... 606/21–25, 27, 606/28; 607/96, 105, 113

[56] References Cited

U.S. PATENT DOCUMENTS

| | | | |
|---|---|---|---|
| 2,319,542 | 5/1943 | Hall | 606/21 |
| 3,929,136 | 12/1975 | Kreeb et al. | 128/303.1 |
| 3,951,152 | 4/1976 | Crandell et al. | 606/25 |
| 4,140,130 | 2/1979 | Storm | 128/404 |
| 4,206,759 | 6/1980 | Shaw | 128/303.1 |
| 4,476,867 | 10/1984 | Parks | 128/400 |
| 4,479,798 | 10/1984 | Parks | 604/175 |
| 4,662,383 | 5/1987 | Sogawa et al. | 128/784 |
| 4,667,658 | 5/1987 | Guibert | 128/24.1 |
| 4,676,258 | 6/1987 | Inokuchi et al. | 128/804 |
| 4,719,919 | 1/1988 | Marchosky et al. | 128/401 |
| 4,791,930 | 12/1988 | Suzuki et al. | 128/399 |
| 4,819,642 | 4/1989 | Andersen et al. | 128/419 R |
| 4,825,880 | 5/1989 | Stauffer et al. | 128/804 |
| 4,869,247 | 9/1989 | Howard et al. | 128/303.1 |
| 4,900,303 | 2/1990 | Lemelson . | |
| 5,190,539 | 3/1993 | Fletcher | 606/25 |

FOREIGN PATENT DOCUMENTS 8303961  11/1983  WIPO ..................................... 606/23

OTHER PUBLICATIONS

Padmakar P. Lele, *Local Tumor Hyperthermia In The 1990's*, pp. 1–10, Reprinted from: *Consensus of Hyperthermia for the 1990's*, H. I. Bicher, Ed., Plenum Pub. Corp.

Hyperthermia, Interstitial, pp. 1583–1593, *Encyclopedia of Medical Devices and Instrumentation*, J. G. Webster (Ed.), John Wiley & Sons, N.Y. vol. 3:1583 et seq. (1988).

P. P. Lele, *Ultrasound Hyperthermia*, pp. 1–44, Reprinted from: *Encyclopedia of Medical Devices and Instrumentation*, J. G. Webster (Ed.), John Wiley & Sons, N.Y. vol. 3: 1599–1612 (1988).

Waterman et al., *Mechanisms of Heat Removal During Local Hyperthermia*, pp. 1049–1055, Nov. 1989, Boston, MA.

Roizin–Towle, *A concept of Thermal Dose is Urgently Needed For the Clinical Application of Hyperthermia*, pp. 557–559, 1989, New York, N.Y.

*Microwaves Are Not Hyperthermia*, pp. 151–162, Dec. 1988, Wembly, Western Australia.

A. C. Steger et al., *Interstitial Laser Hyperthermia: A New Approach To Local Destruction Of Tumours*, pp. 362–365, Aug. 5, 1989, London.

Furse et al., *Three–Dimensional Electromagnetic Power Deposition in Tumors Using Interstitial Antenna Arrays*, pp. 977–986, Oct. 10, 1989 Salt Lake City, Utah.

Padmakar P. Lele, *Advanced Ultrasonic Techniques For Local Tumor Hyperthermia*, pp. 559–575, May 3, 1989, Cambridge, MA.

S. W. Chi, *Heat Pipe Theory and Practice*, pp. 24–25, Washington.

Primary Examiner—Lee S. Cohen
Attorney, Agent, or Firm—Arnold, White & Durkee

[57] ABSTRACT

A catheter that provides precise temperature control for treating diseased tissue. The catheter may use a variety of passive heat pipe structures alone or in combination with feedback devices. The catheter is particularly useful for treating diseased tissue that cannot be removed by surgery, such as a brain tumor.

24 Claims, 7 Drawing Sheets

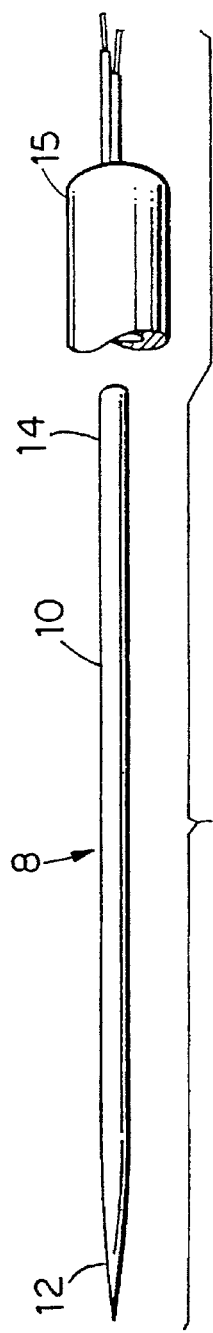
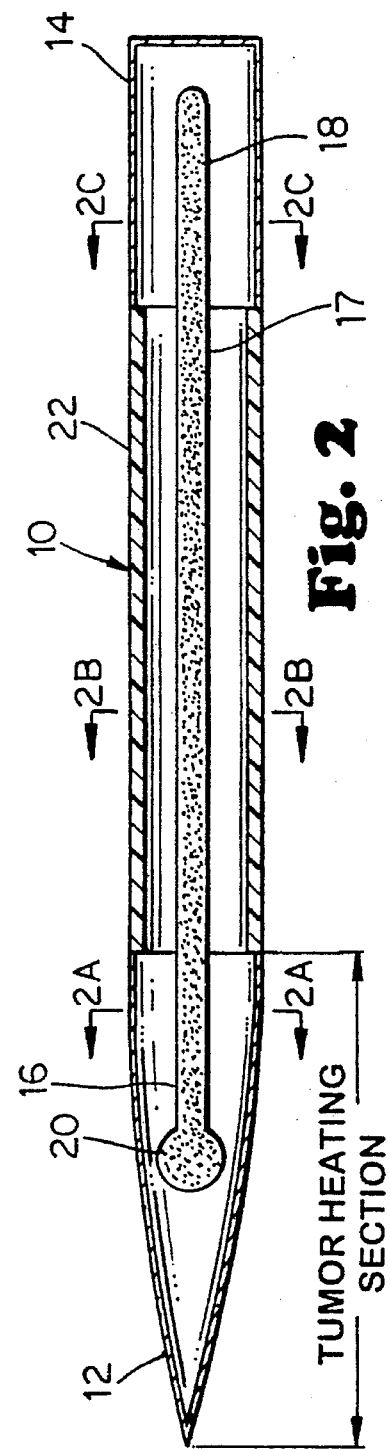
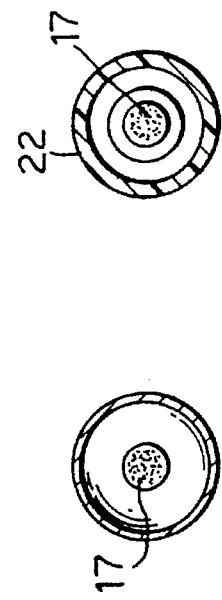
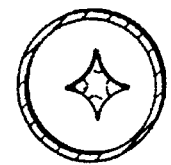
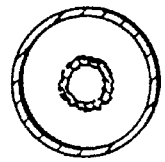

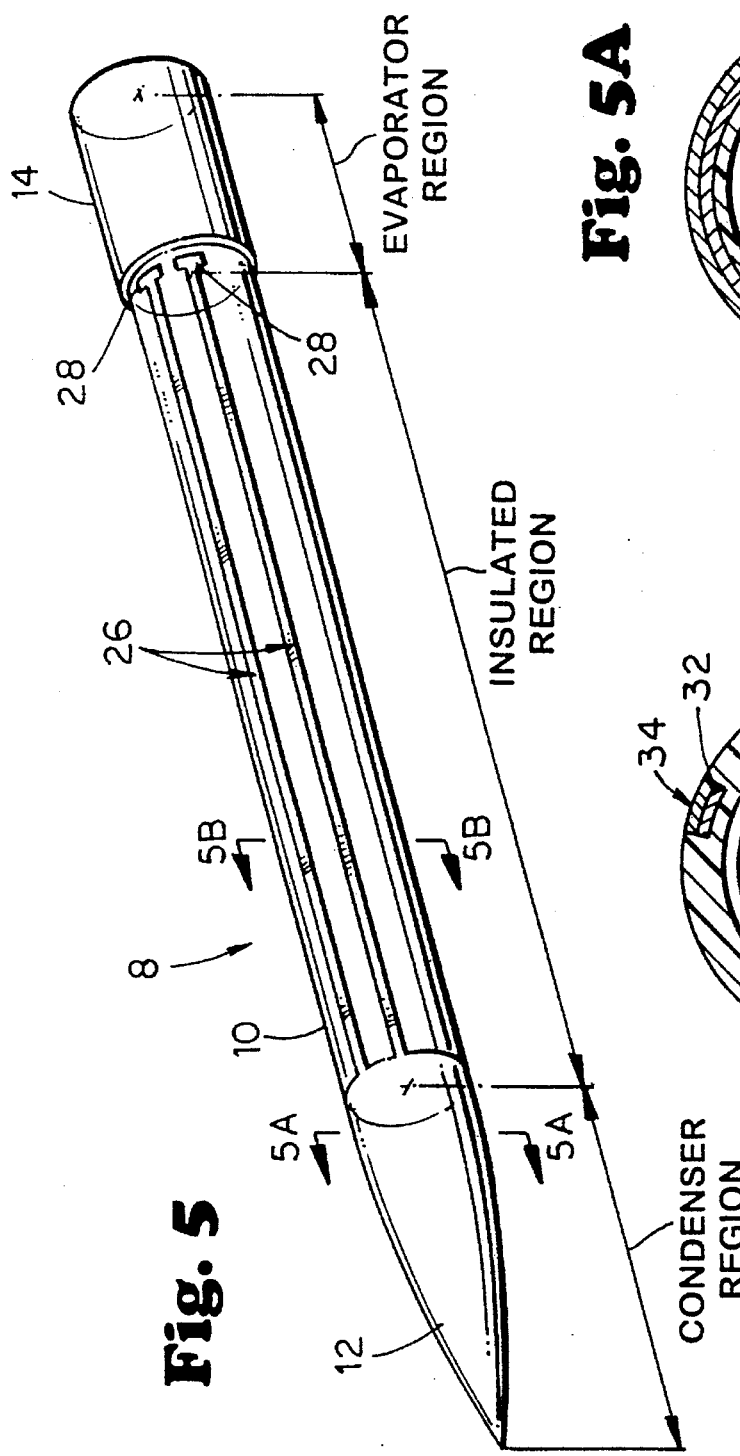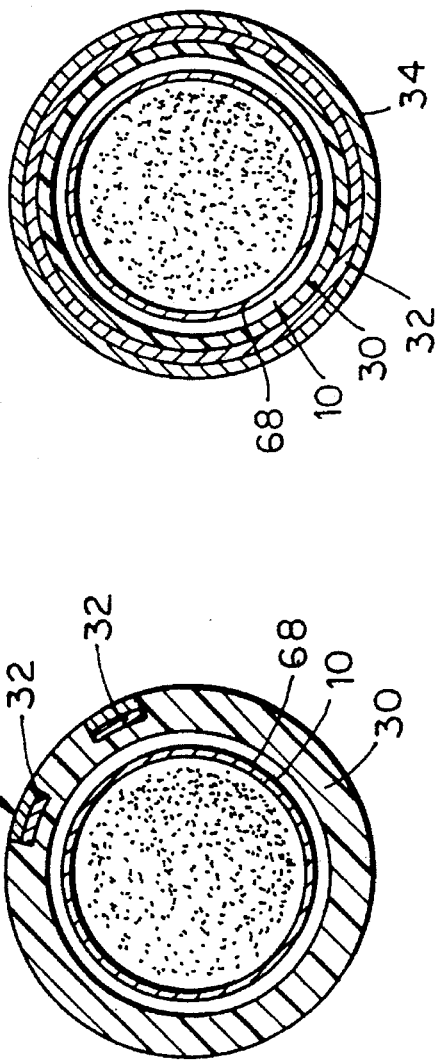

TREATMENT METHOD USING A MICRO HEAT PIPE CATHETER

This application is a divisional of patent application Ser. No. 07/994,551, filed Dec. 21, 1992, now U.S. Pat. No. 5,417,686, which is a continuation-in-part of patent application Ser. No. 550,519, filed Jul. 10, 1990, now U.S. Pat. No. 5,190,539.

BACKGROUND OF THE INVENTION

1. Field of the Invention

The present invention relates generally to medical devices and, more particularly, to temperature control mechanisms and uses for a micro heat pipe catheter.

2. Description of the Related Art

Millions suffer from cancer, and new techniques for cancer treatment are continually being developed. The use of local hyperthermia (elevating the temperature of a cancerous pan of the body to a slightly higher temperature) has received increased attention over the past few years. Heating a cancerous tumor, including the edges of the tumor, to therapeutic temperatures of 42.5° C. (108.5° F.) to 43.0° C. (109.4° F.) for periods of 20 to 30 minutes will in most cases destroy the rapidly growing cancer cells and arrest tumor growth.

Total body temperatures above 41.8° C. (107.2° F.) are detrimental to the functions of the central nervous system, heart, liver, and kidneys, and may even cause histologically obvious damage to tissue cells, whereas tumorcidal effects are generally not observed below 42.5° C. (108.5° F.). At brain temperatures of over 41.8° C. (107.2° F.), the mechanism that regulates body temperature can become incapacitated, and there is danger of 'malignant' or 'runaway' hyperthermia. Further, temperatures of up to 45° C. (113.0° F.) may cause soft tissue necroses and fistulas as well as skin burns. Therefore, accurate temperature control of a localized area is critical to successful hyperthermia.

There is a significant need for development of a simple hyperthermia device which will generate a precisely controllable temperature. The heat should be confined to the diseased region to minimize the risk of damage to the surrounding normal tissue and to preserve normal bodily functions. Local hyperthermia should elevate the temperature of a cancerous tumor to a therapeutic level while maintaining the temperature of the surrounding tissue at, or near normal levels.

Numerous heating methods for tumor treatment have been proposed over the past few decades, and several methods are currently being practiced. These heating techniques may be classified from a clinical point of view as non-invasive and invasive.

Non-invasive hyperthermia techniques focus electromagnetic or ultrasonic energy on the region to be heated. This energy heats the body tissues to the desired temperatures. However, it is not possible to confine this energy to the diseased tissue, and the resulting effect is regional heating rather than local heating. Due to this regional heating, this technique often exhibits large temperature fluctuations due to variations in blood flow and thermal conductivity of the tissue. To better focus the energy to minimize regional heating, the wavelength of the energy beam must be small compared to the tumor's dimensions. An undesirable side effect of reducing the wavelength renders the technique useful for treating diseased areas only a few centimeters into the body. Another limitation is caused by bones being very strong absorbers of ultrasonic waves and air cavities being almost perfect reflectors. Bones may absorb a disproportionate amount of energy, and the reflections cause energy to disperse uncontrollably.

Invasive heating techniques, as compared with non-invasive techniques, are typically better for achieving therapeutic temperature levels without appreciable heating of normal tissues, regardless of the tumor geometry. Invasive heating techniques include the perfusion of the extremities with extracorporally heated blood and the irrigation of the urinary bladder with heated saline. Other invasive heating techniques include placing heating elements directly into the tumor. The use of a number of heating elements facilitates the regulation of temperature throughout the tumor.

Invasive hyperthermia devices include: (1) sets of implanted electrodes connected to a radio frequency generator; (2) combinations of implanted and external electrodes; (3) implanted microwave antennas; and (4) implanted or injected thermoseeds. Each of these invasive devices exhibit drawbacks.

The use of implanted electrodes, while simple, involves placing an array of needles into the tumor and connecting them to an RF generator. The temperature field for such electrodes is very difficult to control, and the volume that can be heated effectively is rather small, requiring many implants. Therefore, this technique is complicated, and the arrangement may result in non-uniform heating.

Electrodes require connections to a power source, and many electrodes are required to treat most tumors. The large number of connection wires or coaxial feed lines associated with the electrodes are cumbersome and may overheat.

Implanting microwave antennas or thermoseeds are probably the most popular invasive heating techniques. Generally, an array of antennas or thermoseeds is implanted in the tumor and left in place for the duration of the treatment. The antennas absorb externally-applied microwave energy, and the thermoseeds absorb externally-applied magnetic energy. Each antenna and thermoseed acts as a small heating unit, transferring heat to the tumor by conduction. The antennas and thermoseeds require careful placement in the tumor to optimize local heating of the tumor. This is particularly so with thermoseeds, because their orientation with respect to the induced magnetic energy determines their heating pattern. Furthermore, because all antennas and thermoseeds are heated to the same temperature by externally-applied energy, areas with poor blood flow may overheat while areas with high blood flow may not attain therapeutic temperatures.

The present invention is directed to overcoming or minimizing one or more of the problems discussed above.

SUMMARY OF THE INVENTION

In accordance with one aspect of the present invention, there is provided a method of treating diseased tissue. The method includes the steps of (1) inserting a needle-like end of a micro heat pipe catheter into the diseased tissue; (2) maintaining the needle-like end of the micro heat pipe catheter within a prescribed temperature range; and (3) thermally insulating a portion of the micro heat pipe catheter to protect healthy tissue from thermal damage.

BRIEF DESCRIPTION OF THE DRAWINGS

The foregoing and other advantages of the invention will become apparent upon reading the following detailed description and upon reference to the drawings in which:

FIG. 1 is a side view of a catheter;

FIG. 2 is a cross-sectional side view of a micro heat pipe catheter;

FIGS. 2A, 2B, 2C, and 2C–I are cross-sectional views taken along lines 2A—2A, 2B—2B, and 2C—2C, respectively in FIG. 2.

FIG. 5 is a perspective view of a micro heat pipe catheter showing the location of the temperature sensing thermocouples;

FIGS. 5A and 5B are cross-sectional views taken along lines 5A—5A and 5B—5B, respectively, in FIG. 5;

Figure 3:
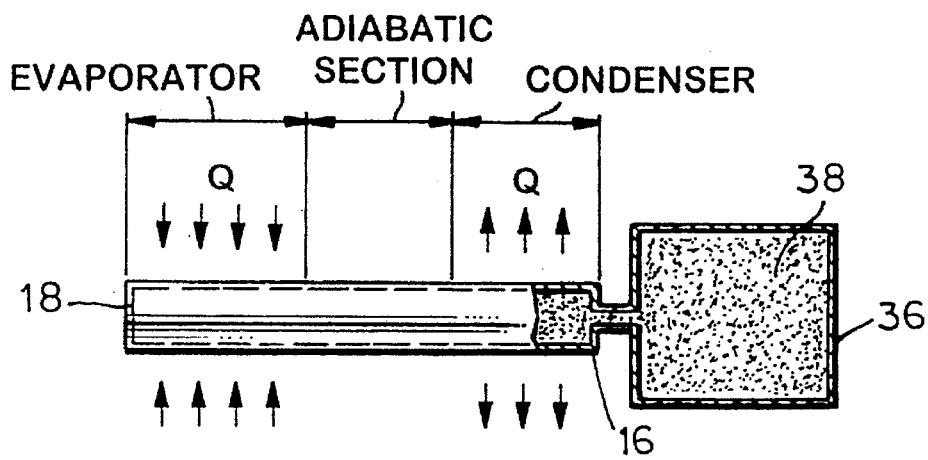
FIG. 3 is a schematic view of a passively-controlled, gas-loaded heat pipe.

The present invention is susceptible to various modifications and alternative forms. Specific embodiments have been shown by way of example in the drawings and will be described in detail herein. However, it should be understood that the invention is not intended to be limited to the particular forms disclosed. Rather, the invention is to cover all modifications, equivalents, and alternatives following within the spirit and scope of the invention as defined by the appended claims.

DETAILED DESCRIPTION OF PREFERRED EMBODIMENTS

Hyperthermia or hypothermia is generally used in addition to surgery, radiation, and chemotherapy, rather than alone as the first line of treatment. Hyperthermia or hypothermia, when used in new or previously treated tumors, is found to produce strong tumorcidal effects. As will become apparent, the catheter disclosed herein replaces some existing hyperthermia or hypothermia treatment techniques for some cancerous tumors and increases the number of individuals who may be treated, because it may be used to treat deep tumors that cannot be effectively treated with other techniques.

Turning now to the drawings and referring initially to FIG. 1, a micro heat pipe catheter 8 is illustrated. The catheter 8 is preferably constructed of stainless steel or other biocompatible material in a manner similar to the construction of hypodermic needles. The catheter 8 has a shaft 10, a needle-like end 12 and a heating or cooling source end 14. The needle-like end 12 is adapted to be inserted through tissue into a tumor. The end 14 is adapted to fit into a temperature control mechanism 15, such as a resistance heater or a cryogenic element.

The temperature control mechanism 15 provides a controllable heating or cooling rate to the end 14 of the catheter 8 to maintain the needle-like end 12 at a substantially constant temperature. For instance, the temperature at the needle-like end 12 preferably ranges from 42.5° C. (108.5° F.) to 43.0° C. (109.4° F.), but this range may vary if another range is deemed therapeutic for the diseased tissue. Controllable heating and cooling sources capable of maintaining temperatures in the appropriate range will operate satisfactorily, and these may include a pre-heated or pre-chilled liquid or a cryogenic fluid.

The catheter is an invasive device. The catheter 8 is inserted directly into a tumor or other diseased region of a body, and the catheter 8 heats or cools the tumor to destroy it. A detachable handle (not shown) may be used for accurate placement, particularly for deep-seated tumors or diseased areas. The handle may be removed and a clip-on temperature control mechanism 15 attached to the end 14 to control the temperature of the needle-like end 12. The temperature of the needle-like end 12 of the catheter 8 is controlled to suit individual tumor requirements. The rate of heat delivered or removed is matched to the thermal conductivity of the tissue and the degree to which the tumor is perfused. The number and depth of the catheters 8 to be inserted into a tumor or diseased tissue depends on the volume and location of the diseased region within the body.

As shown in FIG. 2, an exterior portion of the stainless steel shaft 10 of the catheter 8 is preferably insulated. This portion is preferably inset so that the insulating material 22 can be deposited on the shaft 10 without increasing the diameter of the shaft 10. The insulating material 22 minimizes the radial heat loss through the shaft 10 and minimizes damage to the normal tissue through which the catheter 8 passes. FIG. 2A depicts the cross-section of the channel 18, and FIG. 2B depicts the cross-section of the channel 18 and the insulative layer 22.

FIG. 2 also illustrates the internal structure of a passively controlled, hyperthermic, gas-loaded micro heat pipe that may be used within the catheter 8. The heat pipe includes a channel 17 which has a non-condensible gas reservoir 20. The channel 17 is partially charged with an appropriate working fluid, such as pure water, methanol, ammonia, or nitrogen. The needle-like end 12 houses the condenser 16 of the heat pipe, and the end 14 houses the evaporator 18 of the heat pipe. In applications requiring the removal of thermal energy, such as hypothermia or the cooling of tissue, the roles of condenser and evaporator are reversed.

In most two-phase cycles, the presence of non-condensible gases creates a problem due to the partial blockage of the condensing area. Heat pipes are no exception. During normal operation, any non-condensible gases present are carded to the condenser and remain there, reducing the effective condenser surface area. This characteristic, although normally undesirable, can be used to control the direction and amount of heat transfer and/or the condenser temperature (i.e. the temperature at the tumor).

The heat pipe catheter 8 operates on the thermodynamic principal of essentially constant temperature evaporation and condensation. Therefore, the temperature throughout the length of the catheter 8 is substantially uniform. The temperature variation between the condenser 16 and evaporator 18 regions in the heat pipe may be as little as ±0.1 ° C., depending upon the pressure, temperature, and working fluid used in the heat pipe. When used for hyperthermia (heating the diseased tissue), the catheter 8 is coupled to a heat source that provides heat to the tumor, and when used for hypothermia (cooling the diseased tissue), the catheter 8 is coupled to a cooling source that removes heat from the tumor.

In operation, the working fluid evaporates at the heat-source end 14 and condenses at the tumor-heating section. FIGS. 2C and CI illustrate alternative wicking configurations that carry the condensed working fluid back to the evaporator.

FIGS. 3–8 illustrate a number of heat-transfer control techniques. In these figures, the vertical arrows depict the direction of heat transfer.

FIG. 3 illustrates an passively-controlled, gas-loaded heat pipe mechanism 36 for the catheter 8. In this type of device, the thermal conductance of the heat pipe varies as a function of the "gas front" position. The term "gas front" refers to the vapor/noncondensible gas interface. As the heat available at the evaporator varies, the vapor temperature varies and the noncondensible gas contained within the reservoir expands or contracts, moving the gas front. This in turn results in a variation in the thermal conductance, i.e. as the heat flux increases, the gas front recedes and the thermal conductance increases due to the larger condenser surface area. In this way, the temperature drop across the evaporator and condenser can be maintained fairly constant even through the evaporator heat flux may fluctuate. This will provide a constant temperature at the tumor site, preventing damage to surrounding tissue.

While in most applications heat pipes operate in a passive manner, adjusting the heat flow rate to compensate for the temperature difference between the evaporator and condenser, several active control schemes have been developed. Most notable among these are: (i) gas-loaded heat pipes with a feedback system, (ii) excess-liquid heat pipes, (iii) vapor flow-modulated heat pipes, and (iv) liquid flow-modulated heat pipes.

In the embodiment of FIG. 3, the gas volume at the reservoir end 38 of the heat pipe 36 is controlled passively by expansion and contraction of the non-condensible gas in the reservoir 38. Active control can be achieved by heating or cooling the reservoir 38. The reservoir 38 is heated or cooled by coupling a temperature control mechanism 15 to a thin resistive coating 40 that is disposed, preferably by vapor deposition, on the shaft 10 of the catheter 8. The coating 40 is preferably nichrome.

Figure 4:
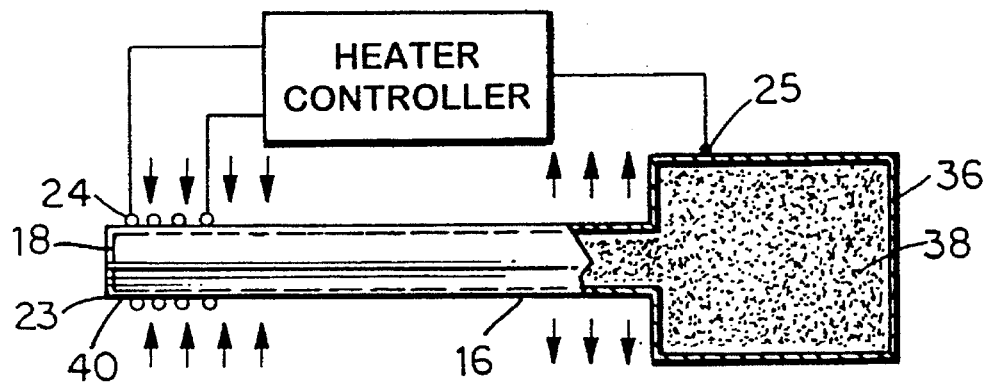
FIG. 4 is a schematic view of an actively-controlled, gas-loaded heat pipe.

An actively controlled temperature control technique employs a temperature sensing device at the needle-like end 12 of the catheter 8 to provide a feedback signal to the temperature control mechanism 15. FIG. 4 illustrates an actively-controlled, gas-loaded heat pipe 23 in which the gas volume at the reservoir end can be 11 controlled externally. In this embodiment, a temperature-sensing device 25 at the condensor 36 provides a signal to the temperature control means, which is illustrated in FIG. 4 as an evaporator heater 24, via a heater controller 27. The heater 24, when activated, can heat the gas contained in the evaporator 18, causing it to expand and thereby reducing the condenser area.

FIG. 5 illustrates such the device 25 as a temperature-sensing thermocouple 26 for use with either hyperthermic or hypothermic micro heat pipe catheters. FIGS. 5A and 5B illustrate the corresponding cross-sections. The temperature-sensing thermocouple 26 may be fabricated through vapor deposition, chemical deposition, thermal deposition, sputter deposition, plasma spraying or other similar techniques of depositing dissimilar metals on a portion of the shaft 10. The thermocouple mechanism 26 is created by first depositing an electrically insulating layer 30, typically an oxide, onto the shaft 10 and the needle-like end 12. A thin layer of electrically conductive material 32, such as copper, is deposited on the electrically insulating layer 30. A second thin layer of dissimilar electrically conductive material 34, such as iron, is then deposited over the first layer of material 32. Electrical connections, terminating in contact pads 28, from each of these two layers are fabricated by depositing these materials along the shaft 10 toward the end 14. The layers of material 30, 32, and 34 are thin enough that they do not significantly increase the diameter of the catheter 8.

Once the thermocouple 26 is formed, the difference in the electrical potential at the junction of the materials 32 and 34 is correlative to the temperature at the needle-like end 12 of the catheter 8. Thus, this temperature signal can be delivered to the temperature control mechanism 15 to more precisely control the temperature at the needle-like end 12 of the catheter 8. The temperature sensing thermocouple 26 can be used with any of the passive temperature control mechanisms described with reference to FIGS. 5, 6, 7 and 8.

Figure 6:
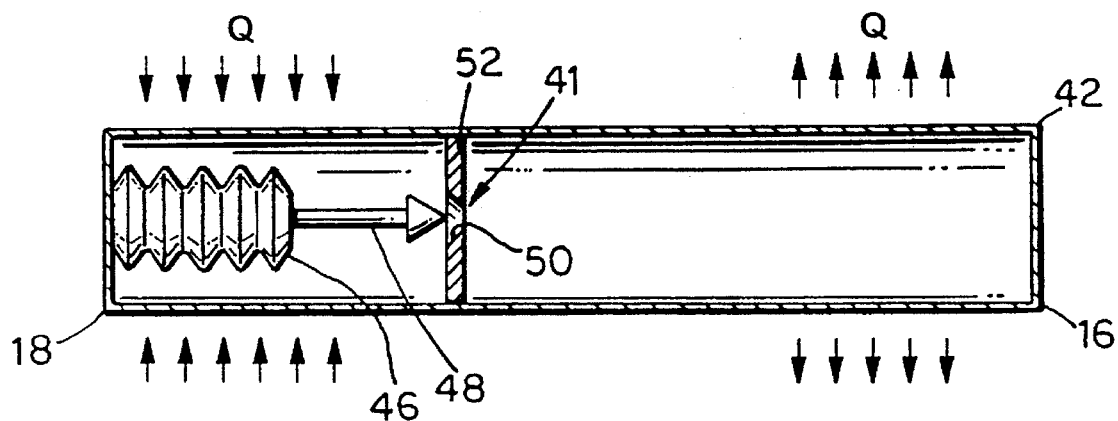
FIG. 6 is a schematic view of a vapor-modulated variable conductance heat pipe.

FIG. 6 illustrates a passively-controlled, vapor-flow modulated heat pipe mechanism 42 for the catheter 8 and which is particularly suited for hyperthermic treatments. Excess-liquid heat pipes operate in much the same manner as gas-loaded heat pipes but utilize excess working fluid to block portions of the pipe and control the condenser size or prevent reversal of heat transfer. Vapor-flow-modulated heat pipes utilize a throttling valve to control the amount of vapor leaving the evaporator. In this embodiment, a throttling valve 41 controls the amount of vapor leaving the evaporator 18. An increase of the temperature of the vapor in the evaporator 18 causes the baffle 46 containing the control fluid to expand. This in turn closes down the throttling valve 41, by pushing the plunger 48 into the opening 50 of the flange 52, and reduces the flow of vapor to the condenser 42. This embodiment is particularly useful in situations where the evaporator temperature varies and a constant condenser temperature is desired.

Figure 7:
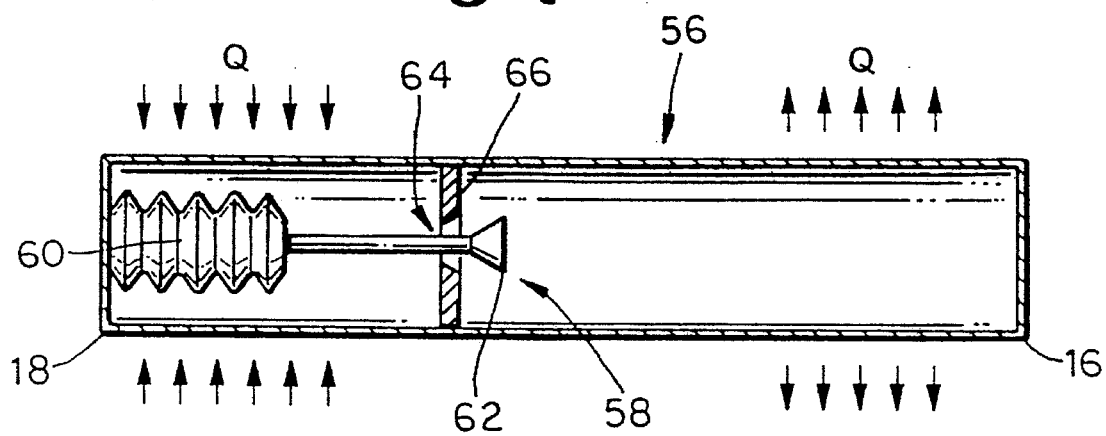
FIG. 7 is a schematic view of another vapor-modulated variable conductance heat pipe.

FIG. 7 illustrates another passively-controlled, vapor-flow modulated heat pipe 56 for use with the catheter 8 and which is particularly suited for hypothermic treatments. A throttling valve 58 controls the amount of vapor leaving the evaporator 18. An increase of the temperature of the vapor in the evaporator 18 causes the baffle 60 containing the control fluid to expand. This causes the valve 58 to open by pushing the plunger 62 out of the opening 64 of the flange 66.

Figure 8:
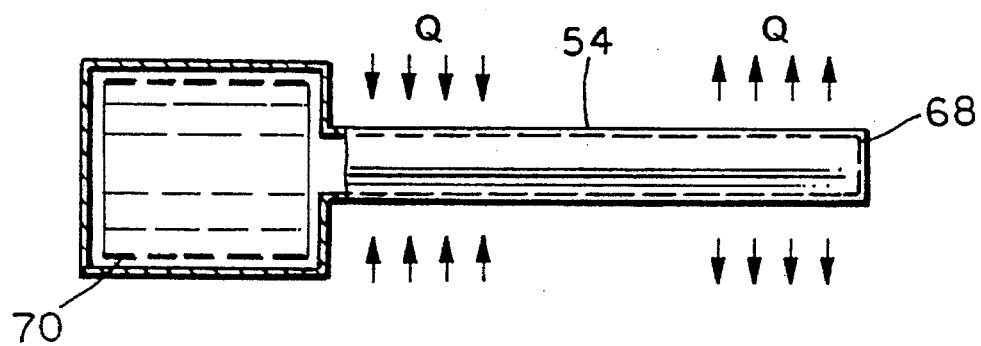
FIG. 8 is a schematic view of a liquid-modulated heat pipe.

FIG. 8 illustrates a passively-controlled, liquid-flow modulated heat pipe 54 for the catheter 8. In this embodiment, two separate heating structures are utilized. A first heating structure 68 transports liquid from the evaporator 18 to the condenser 16. A second heating structure 70 serves as a liquid trap. As the temperature gradient is reversed, the liquid moves into the trap 70 and starves the evaporator 18 of fluid, thus regulating the temperature of the condenser 16 to maintain the tumor at the predetermined temperature and to prevent damage to the surrounding tissue.

The catheter 8 may be used to treat many varieties of cancer. One particularly attractive feature of the catheter 8 is its ability to treat forms of cancer currently untreatable by invasive methods and devices. The catheter 8 may be made thin enough to minimize hemorrhaging of the healthy tissue through which it passes, and its shaft 10 is insulated to further reduce damage to healthy tissue. In each case, the needle-sharp end 12 of the catheter 8 is inserted into the diseased tissue 72. A heating or cooling source 15 is externally coupled to the end 14 to heat or cool the working fluid of the catheter 8.

Figure 9:
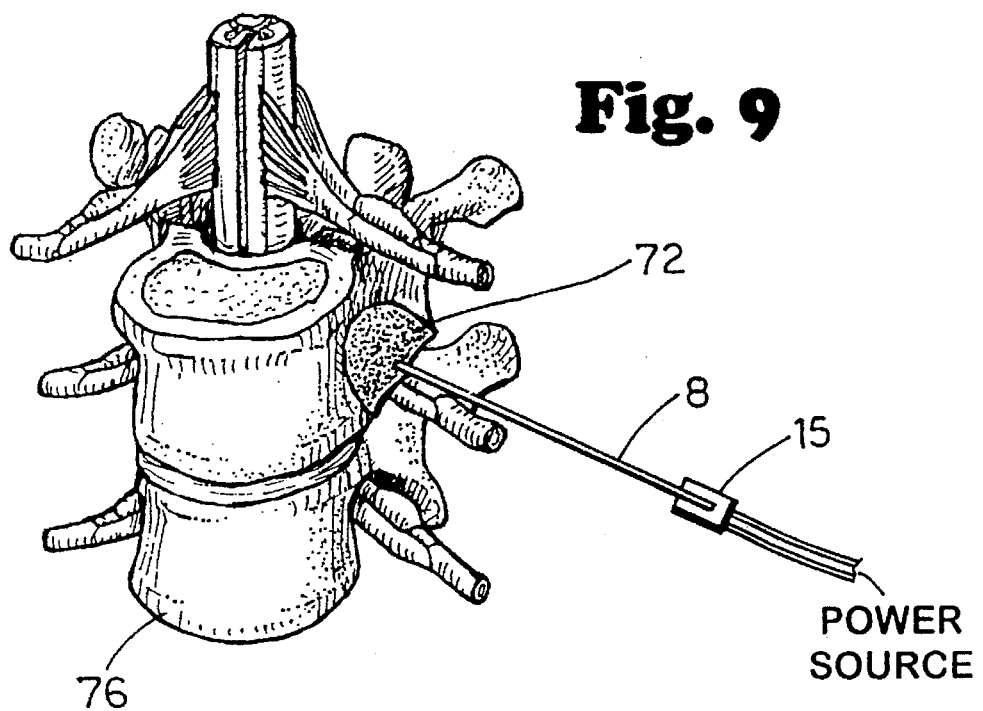
FIG. 9 illustrates a method of treating diseased tissue located near the spinal cord.

FIG. 9 illustrates a method of treating diseased tissue 72 located near the spinal cord 76. A tumor near the spinal cord may not be amenable to surgery due to the danger of severing nerves. However, the catheter 8 may be inserted into a tumor near the spinal cord with little danger of severing nerves.

Figure 10:
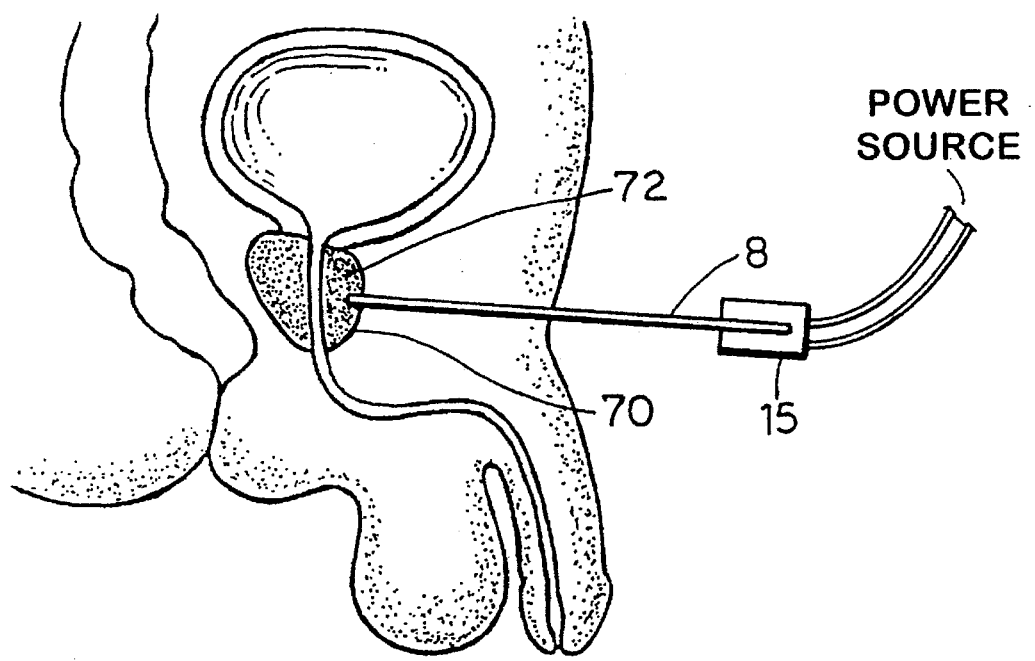
FIG. 10 illustrates a method of treating diseased tissue located in the prostrate gland.
Figure 11:
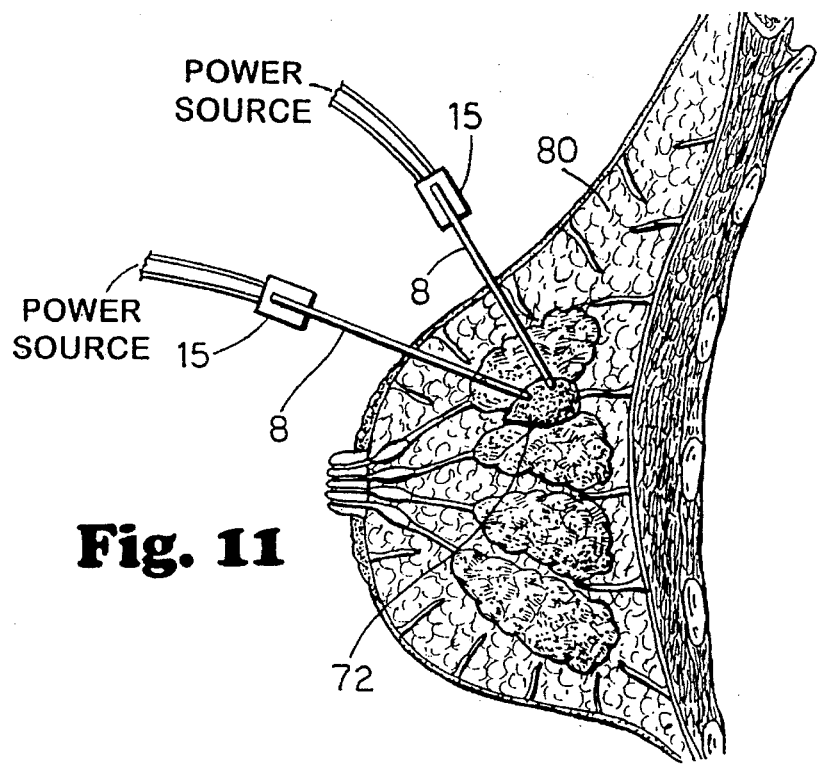
FIG. 11 illustrates a method of treating diseased tissue located in the breast.

FIG. 10 illustrates a method of treating diseased tissue 72 located in the prostrate gland 74, and FIG. 11 illustrates a method of treating diseased tissue 72 located in the breast 80. Although these tumors are generally treatable with surgical methods, the catheter 8 may be used instead to destroy these types of tumors without surgery.

Figure 12:
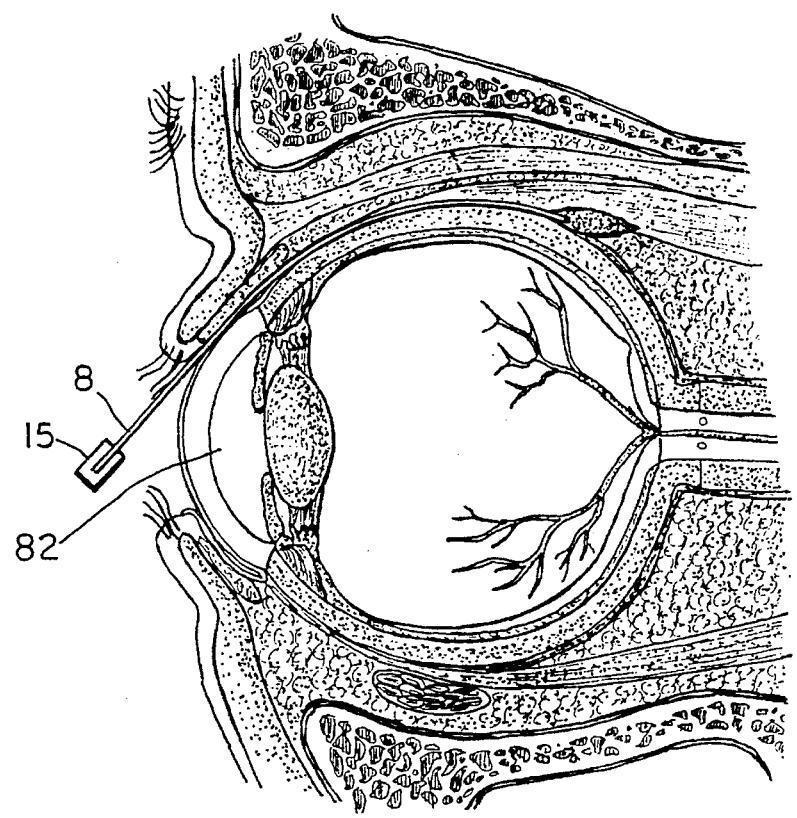
FIG. 12 illustrates a method of treating diseased tissue located near the eye.

FIG. 12 illustrates a method of treating diseased tissue 72 located near the eye 82. Like the spinal cord, surgery near the eye can also pose problems, so the catheter 8 can be used to destroy the tumor and avoid surgery. It should be noticed that the catheter 8 may be curved or flexible so that it can be inserted between the eyelid and the eye to reach the tumor 72 with the minimum of tissue penetration.

Figure 13:
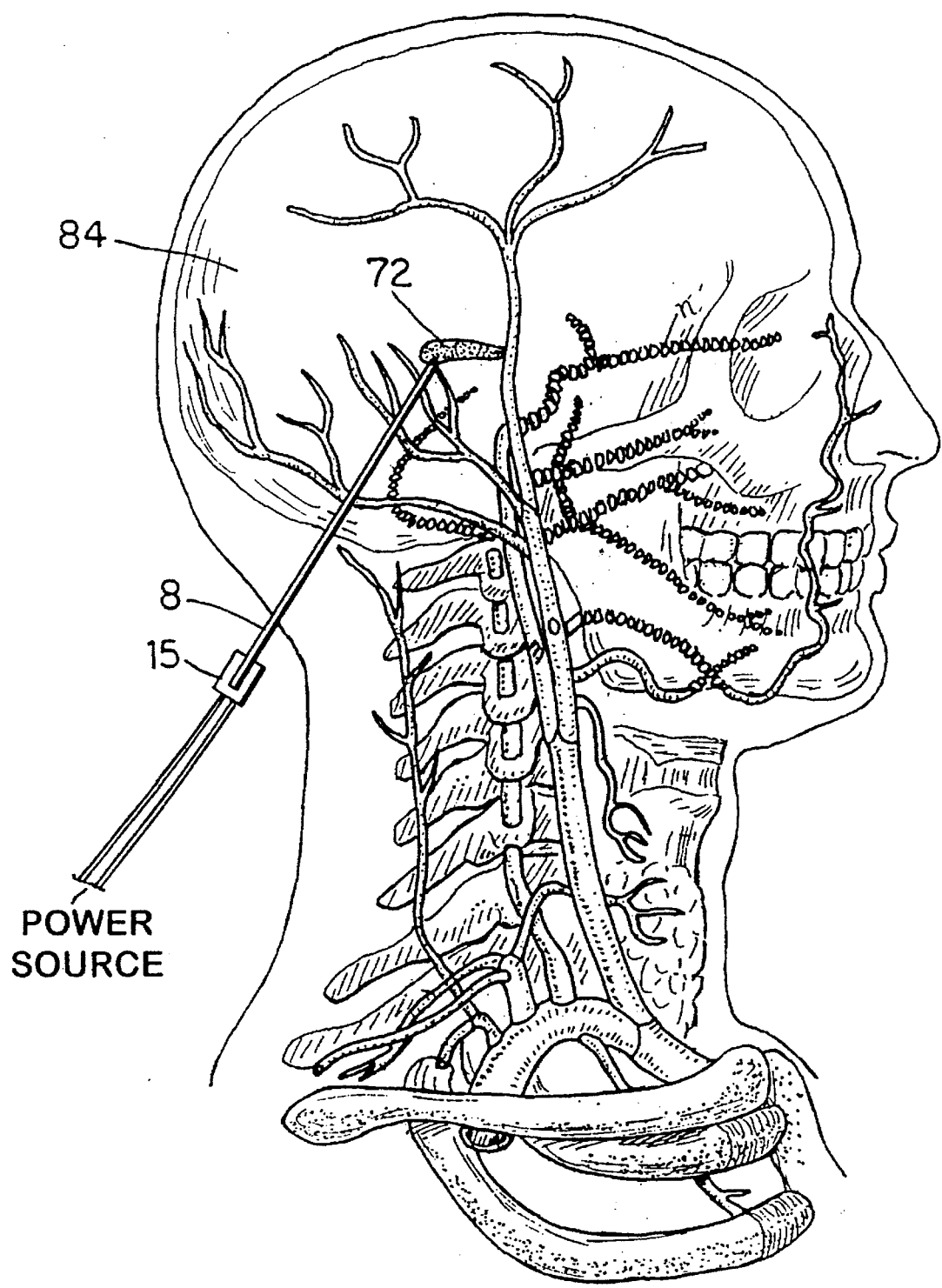
FIG. 13 illustrates a method of treating diseased tissue located in the brain.

FIG. 13 illustrates a method of treating diseased tissue 72 located in or near the brain 84. Brain tumors must be located near the skull before surgery can be considered. Methods such as radiation therapy and chemotherapy are typically used to treat deeper tumors, and often without success. However, the catheter 8 may be inserted through brain tissue with minimal damage due to the catheter's small diameter and insulative covering. A hole is drilled in the skull and the catheter is inserted through the hole into the diseased tissue 72. Because the temperature of the needle-like end 12 of the catheter 8 can be controlled so precisely, the tumor can be therapeutically treated while the damage to surrounding tissue is minimized.

As is evident from the above descriptions, the catheter 8 delivers heat to or removes heat from a tumor or diseased region and maintains the tumor at a substantially constant temperature. The catheter 8 is a simple device that requires no complex external equipment, high voltages, or wave energy transmissions. The catheter 8 may be either actively controlled through a self-contained unit and/or passively controlled using one of several heat-pipe control mechanisms. The catheter 8 may be fabricated in different lengths and different diameters for specific tumor locations and volumes. For specific applications, the catheter 8 may be curved or flexible to facilitate its insertion around an obstruction or to avoid the invasion of a particular organ. Treatment of a cancerous tumor or diseased area may require a number of catheters 8, depending upon the volume, location, and perfusion of the tumor. Finally, the catheter 8 may be designed to operate at a preselected temperature, and the precise temperature control minimizes the amount of information required about the size, shape and density of the tumor being treated.

What is claimed is:

1. A method of treating diseased tissue comprising the steps of:

inserting a needle-like end of a micro heat pipe catheter into said diseased tissue;

maintaining said needle-like end of said micro heat pipe catheter within a prescribed temperature range; and using an insulative coating to thermally insulate a portion of said micro heat pipe catheter to protect healthy tissue from thermal damage.

2. The method of claim 1 wherein the diseased tissue is a cancerous tumor.

3. The method of claim 1 wherein the diseased tissue is a non-cancerous tumor.

4. The method of claim 1 wherein the diseased tissue is located in the brain.

5. The method of claim 4 wherein said step of inserting comprises:

drilling a hole in a skull; and inserting said catheter through said hole and said brain to said diseased tissue.

6. The method of claim 1 wherein the diseased tissue is located in or near the lungs.

7. The method of claim 1 wherein the diseased tissue is located in the breast.

8. The method of claim 1 wherein the diseased tissue is located in or near the prostate gland.

9. The method of claim 1 wherein the diseased tissue is located near the spinal column.

10. The method of claim 1 wherein the diseased tissue is located near the eye.

11. The method of claim 1 wherein the diseased tissue is located in or near the ovaries.

12. The method of claim 1 further comprising the steps of inserting multiple micro heat pipe catheters into said diseased tissue and repeating the steps of maintaining and using for each of said multiple micro heat pipe catheters.

13. The method of claim 1 wherein the step of maintaining comprises maintaining said temperature range about a temperature of 42.75° C.

14. The method of claim 1 wherein the step of maintaining comprises maintaining a temperature range of ±0.25° C. about a prescribed temperature.

15. The method of claim 1 wherein the step of maintaining comprises maintaining a temperature range of ±0.1 ° C. about a prescribed temperature.

16. The method of claim 1 wherein the step of inserting comprises inserting said micro heat pipe catheter by piercing said diseased tissue and any healthy tissue covering said diseased tissue with said needle-like end of said micro heat pipe catheter.

17. A method of treating diseased tissue comprising the steps of:

inserting a needle-like end of a micro heat pipe catheter into said diseased tissue leaving a portion of said micro heat pipe catheter extending from said tissue; and placing a controllable thermal transfer element on said extending portion of said micro heat pipe catheter, said thermal transfer element maintaining said needle-like end of said micro heat pipe catheter within a prescribed temperature range.

18. The method of claim 17 wherein the said temperature range is centered about a temperature of 42.75° C.

19. The method of claim 17 wherein said thermal transfer element maintains said needle-like end of said micro heat pipe catheter within a temperature range of ±0.25° C. about a prescribed temperature.

20. The method of claim 17 wherein said needle-like end of said micro heat pipe catheter is maintained within a temperature range of ±0.1° C. about a temperature of said extending portion of said micro heat pipe catheter.

21. The method of claim 17 wherein the step of inserting comprises inserting said micro heat pipe catheter by piercing said diseased tissue and any healthy tissue covering said diseased tissue with said needle-like end of said micro heat pipe catheter.

22. A method of treating diseased tissue comprising the steps of:
   inserting a needle-like end of a micro heat pipe catheter into said diseased tissue; and
   maintaining said needle-like end of said micro heat pipe catheter within a temperature range about 42.75° C.

23. The method of claim 22 wherein the step of maintaining comprises maintaining a temperature range of ±0.25° C. about 42.75° C.

24. The method of claim 22 wherein the step of inserting comprises inserting said micro heat pipe catheter by piercing said diseased tissue and any healthy tissue covering said diseased tissue with said needle-like end of said micro heat pipe catheter.

* * * * *

UNITED STATES PATENT AND TRADEMARK OFFICE
CERTIFICATE OF CORRECTION

PATENT NO. : 5,591,162
DATED : January 7, 1997
INVENTOR(S) : Leroy S. Fletcher; George P. Peterson It is certified that error appears in the above-indentified patent and that said Letters Patent is hereby corrected as shown below:

At Column 5, line 41, both occurrences of "reservoir 38", should be --evaporator 18--

At Column 5, line 51, "11" should be deleted.

Signed and Sealed this

Twenty-ninth Day of April, 1997

Attest:

BRUCE LEHMAN

Attesting Officer

Commissioner of Patents and Trademarks